(12) United States Patent
Bauer et al.

(10) Patent No.: US 12,121,444 B2
(45) Date of Patent: *Oct. 22, 2024

(54) IMPLANTABLE DRUG ELUTING DEVICE COMPRISING A MICROPOROUS STRUCTURE

(71) Applicant: WALDEMAR LINK GMBH & CO. KG, Hamburg (DE)

(72) Inventors: Eckhard Bauer, Kiel (DE); Helmut D. Link, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/321,797

(22) Filed: May 23, 2023

(65) Prior Publication Data

US 2023/0285155 A1     Sep. 14, 2023

Related U.S. Application Data

(63) Continuation of application No. 16/755,217, filed as application No. PCT/EP2018/077735 on Oct. 11, 2018, now Pat. No. 11,696,830.

(30) Foreign Application Priority Data

Oct. 11, 2017   (EP) ..................................... 17195993

(51) Int. Cl.
*A61F 2/30*        (2006.01)
*A61F 2/02*        (2006.01)
(Continued)

(52) U.S. Cl.
CPC ............ *A61F 2/30771* (2013.01); *A61F 2/34* (2013.01); *A61F 2002/30784* (2013.01);
(Continued)

(58) Field of Classification Search
None
See application file for complete search history.

(56) References Cited

U.S. PATENT DOCUMENTS 4,207,715 A * 6/1980 Kitrick ................. E04B 1/3211
                                                        52/745.07
6,282,849 B1 * 9/2001 Tuczek ..................... E04B 1/32
                                                        52/648.1
(Continued)

FOREIGN PATENT DOCUMENTS

CN      200980747 Y    11/2007
CN      101437467 A    5/2009
(Continued)

OTHER PUBLICATIONS

Notification of Grant mailed Sep. 14, 2022 in connection with Chinese Patent Application No. 201880066468.7, filed Oct. 11, 2018, 7 pgs. (including translation).
(Continued)

*Primary Examiner* — Ann Schillinger
(74) *Attorney, Agent, or Firm* — Chiesa Shahinian & Giantomasi PC

(57) ABSTRACT

Implantable drug-eluting device comprising a microporous structure having regularly arranged pores in at least two different uniform sizes, and manufacturing method. The pores are configured for receiving a drug and are being connected by interconnections. Interconnections originating from pores of a first size have a first elution area and interconnections originating from pores of a second size have a second elution area. The interconnections convey the drug to a surface of the device for elution to surrounding tissue. The ratio between the first and the second elution areas is predefined and selectable. The differently sized elution areas provide for different outflow rates. This allows for simple but reliable dispensing of drugs at positively
(Continued)

Figure 1:
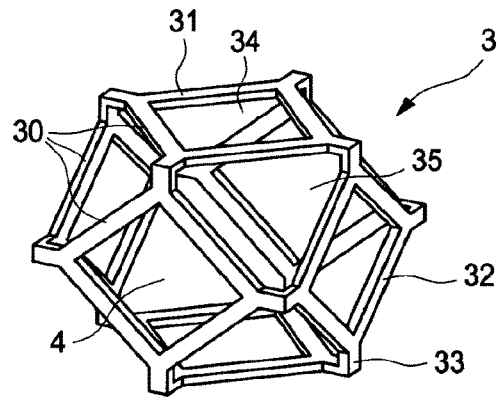

controlled and well determined rates. Particularly, this enables a single implantable device to dispense drugs over preselectable durations of time, like short-term or long-term.

17 Claims, 3 Drawing Sheets

(51) Int. Cl.
    *A61F 2/28*         (2006.01)
    *A61F 2/34*         (2006.01)

(52) U.S. Cl.
    CPC ............... *A61F 2002/30838* (2013.01); *A61F 2002/30884* (2013.01); *A61F 2002/3093* (2013.01); *A61F 2002/30985* (2013.01); *A61F 2250/0067* (2013.01)

(56) References Cited

U.S. PATENT DOCUMENTS

| | | | |
|---|---|---|---|
| 6,702,848 B1* | 3/2004 | Zilla | A61F 2/06 623/1.39 |
| 8,052,744 B2 | 11/2011 | Girton | |
| 8,429,874 B2* | 4/2013 | Schneider | E04B 1/32 52/653.1 |
| 9,668,863 B2* | 6/2017 | Sharp | B33Y 10/00 |
| 9,857,026 B1* | 1/2018 | Hoberman | E04B 7/107 |
| 10,278,823 B1* | 5/2019 | Xue | A61F 2/3662 |
| 10,443,233 B2* | 10/2019 | von Gonten | E04H 9/0215 |
| 10,465,376 B1* | 11/2019 | Hoberman | E04B 1/35 |
| 10,793,683 B2* | 10/2020 | Johnson | C08G 83/008 |
| 10,851,283 B2* | 12/2020 | Potapenko | C09K 8/62 |
| 11,045,297 B2* | 6/2021 | Carpenter | A61F 2/0077 |
| 11,410,746 B2* | 8/2022 | Veneziano | G16B 15/00 |
| 11,696,830 B2* | 7/2023 | Bauer | A61L 27/56 623/22.21 |
| 2003/0045927 A1* | 3/2003 | Zilla | A61L 27/48 623/1.46 |
| 2005/0112397 A1 | 5/2005 | Rolfe et al. | |
| 2006/0085009 A1* | 4/2006 | Truckai | A61L 27/14 606/94 |
| 2006/0147332 A1* | 7/2006 | Jones | A61F 2/3094 148/513 |
| 2007/0071789 A1 | 3/2007 | Pantelidis et al. | |
| 2007/0198040 A1* | 8/2007 | Buevich | A61L 31/10 606/151 |
| 2009/0214601 A1 | 8/2009 | Chappa et al. | |
| 2010/0036502 A1 | 2/2010 | Svrluga et al. | |
| 2010/0137990 A1* | 6/2010 | Apatsidis | A61F 2/4425 606/301 |
| 2010/0174377 A1* | 7/2010 | Heuer | A61L 27/30 435/395 |
| 2010/0291401 A1* | 11/2010 | Medina | B23K 26/32 219/121.66 |
| 2011/0076316 A1* | 3/2011 | Sivananthan | A61P 19/02 435/395 |
| 2011/0172798 A1* | 7/2011 | Staiger | A61L 27/56 700/98 |
| 2012/0010636 A1* | 1/2012 | Boey | A61L 31/10 606/151 |
| 2012/0191200 A1 | 7/2012 | Choren | |
| 2012/0265167 A1* | 10/2012 | Simonson | A61B 17/7095 604/506 |
| 2013/0211533 A1* | 8/2013 | Fonte | A61F 2/30767 623/22.4 |
| 2013/0304233 A1 | 11/2013 | Pean et al. | |
| 2013/0325142 A1 | 12/2013 | Hunter et al. | |
| 2014/0072608 A1 | 3/2014 | Logothetidis et al. | |
| 2014/0114435 A1 | 4/2014 | Carpenter et al. | |
| 2014/0363481 A1* | 12/2014 | Pasini | A61F 2/32 703/1 |
| 2017/0095337 A1* | 4/2017 | Pasini | A61F 2/36 |
| 2017/0319345 A1 | 11/2017 | Faccioli et al. | |
| 2018/0021139 A1* | 1/2018 | Spivack | A61C 8/0012 606/331 |
| 2018/0193152 A1 | 7/2018 | Bauer | |
| 2018/0193530 A1* | 7/2018 | Barbas | A61F 2/30767 |
| 2018/0280140 A1* | 10/2018 | Jones | A61F 2/2846 |
| 2020/0375726 A1* | 12/2020 | Limem | A61F 2/12 |

FOREIGN PATENT DOCUMENTS

| | | | |
|---|---|---|---|
| CN | 101610740 A | 12/2009 | |
| CN | 101810522 A | 8/2010 | |
| CN | 105102009 A | 11/2015 | |
| CN | 106999285 A | 8/2017 | |
| EP | 0963834 A1 * | 6/1998 | ............... A61F 2/30 |
| EP | 1891995 A1 | 2/2008 | |
| EP | 2328511 A2 | 6/2011 | |
| JP | 2010503485 A | 2/2010 | |
| JP | 2012501228 A | 1/2012 | |
| WO | 2014143719 A1 | 9/2014 | |
| WO | 2017005514 A1 | 1/2017 | |
| WO | 2018200816 A1 | 11/2018 | |

OTHER PUBLICATIONS

Notice of Reasons for Refusal mailed Aug. 9, 2022, in connection with Japanese Patent Application No. 2020-520117, 14 pgs. (translation included).

Office Action issued in corresponding Chinese Application No. 201880066468.7 dated Aug. 13, 2021 and its English Translation.

English Translation of the Search Report issued in Chinese Application No. 201880066468.7.

Office Action mailed Feb. 7, 2023 in connection with Chinese patent application No. 21880664687, filed Oct. 11, 2018, 13 pgs. (including translation).

Office Action issued in corresponding European Application Number 17195993 .5.

English Translation of the International Preliminary Report on Patentability issued on Apr. 14, 2020 in corresponding International Application No. PCT/EP2018/077735.

Boetker Johan et al., "Modifying Release Characteristics from 3D Printed Drug-Eluting Products," European Journal of Pharmaceutical Sciences, Elsevier, Amsterdam, NL, vol. 90, Mar. 15, 2016 (Mar. 15, 2016), pp. 47-52, XP029616197.

International Search Report and Written Opinion mailed Dec. 12, 2018 in corresponding International Application No. PCT/EP2018/ 077735.

\* cited by examiner

IMPLANTABLE DRUG ELUTING DEVICE COMPRISING A MICROPOROUS STRUCTURE

CROSS-REFERENCE TO RELATED APPLICATIONS

This application is a Continuation of prior-filed U.S. patent application Ser. No. 16/755,217, filed Apr. 10, 2020, which is the National Stage entry under 35 U.S.C. § 371 of International Application No. PCT/EP2018/077735, filed on Oct. 11, 2018, which claims the benefit of priority under 35 U.S.C. § 119 of European Patent Application No. 17195993.5, filed Oct. 11, 2017, the disclosure of all of which are herein incorporated by reference in their entireties.

The invention relates to an implantable drug eluting device comprising a microporous structure, the microporous structure comprising regularly arranged pores in at least two different uniform sizes, a first size and a second size. The pores are configured for receiving the drug and are being connected by interconnections. The interconnections originating from the pores of the first size have a first elution area, and the interconnections originating from the pores of the second size have a second elution area. The interconnections are configured to convey the drug from the pores to a surface of the microporous structure for elution to surrounding tissue via the elution area.

For implanting artificial devices, like endoprosthesis, artificial joints or other implants two kinds of post-surgery complications need to be addressed. The first issue is how to promote bone ingrowth in order to achieve a rapid and proper stabilization of the implant. So bone ingrowth has to be promoted. On the other hand, the second issue is that any risk of infection must be minimized. Infection not only hampers a proper ingrowth of the device itself, but also brings the risk of adverse reactions within the patient's body. Therefore, it creates a major hazard to health of the patient. So it is paramount to reduce infection risk. It is thus desirable to provide implants which promote bone ingrowth at one hand and are capable of reducing infection risk at the other hand.

An implant having porous surface for storage of drugs that may flow out of the pores post-surgery is known by US patent application published as US 2009/0112310 A1. This document provides an implant in which pores are created close to the surface by etching with an acid. Pores of a second size are created subsequently in a similar manner. A drawback of this approach is that the etching provides poor control only with respect to distribution of the pores and their relative arrangement. As an inherent disadvantage of this subtractive approach by means of etching, it is difficult to control density and depth of the pores. As a result, it is quite difficult to achieve a proper control of drug elution.

It is an object of the invention to provide an improved implantable device that allows for better controlled drug elution, in particular in terms of slow drug elution.

The solution according to the invention resides in the features of the independent claims. Advantageous embodiments are the subject matter of the dependent claims.

An implantable drug-eluting device comprising a microporous structure, the microporous structure comprising regularly arranged pores in at least two different uniform sizes, a first size and a second size, wherein the pores are configured for receiving a drug and are being connected by interconnections, the interconnections originating from the pores of the first size having a first elution area and the interconnections originating from the pores of the second size having a second elution area, are configured to convey the drug to a surface of the microporous structure for elution to surrounding tissue via the elution areas, wherein according to the invention a ratio between the first elution area and the second elution area is predefined and selectable.

According to the invention, at least two different kinds of pores are being formed regularly, said kinds of pores having interconnections with differently sized elution areas. Due to the differently sized elution areas, the outflow rate of a drug positioned within the pores differ between the kinds of pores, depending whether the drug is located in a first kind of pores having a first elution area or within a second kind of pores having interconnections with differently sized second elution area. The elution area determines a rate of elution of any drug in the respective pore.

This allows for a simple but reliable dispensing of drugs at positively controlled and well determined rates. Particularly, this enables the implantable device according to the invention to being equipped with drugs that shall be dispensed over a preselectable duration of time, like short-term or long-term. An example for drugs for short-term dispensing would be anti-infection drugs in order to combat any infection that may arise due to the process of implanting, and an example for drugs for long-term dispensing would be a bone-ingrowth promoting drugs in order to ensure proper long-term fixation of the implant.

Advantageously, the ratio between the volume of the pores of the first size and the pores of the second size is predefined and selectable, too. By virtue of this additional control with respect to the size of the drug storage in the pores and consequently to the length of time of dispensing is gained.

In a preferred embodiment that microporous structure is made of regularly arranged unit cells of a modified cuboctaeder type. Such structure is enabled to provide pores of two different types and sizes, each type of pore having its distinctly shaped and sized elution area. Preferably, the microporous structure is a modified cuboctaeder comprising square and triangle type subelements, the square type subelements being connected to neighboring square elements by additional angled struts. Providing said angled struts allows for an easy modification of the ratio between the area of the square subelements at one hand and the area of the triangle shape subelements at the other hand, namely by varying the length of the diagonal struts.

The invention has found that in a preferred embodiment said ratio of elution area is substantially equal but the ratio of the volumes of pores differs largely, namely by at least two. This allows for fine-tuned dispensing of two different drugs stored in the different kinds of pores. It is of particular advantage in cases wherein the kinds of drugs interact with each other in some manner. Conversely, in another preferred embodiment said ratio of the volumes may be smaller than two, i.e., rather similar, but the ratio of the elution area differs by at least four. This allows for a high flow rate dispensing of one kind of drug initially immediately subsequently following to implantation.

Advantageously, said unit cells and eventually the microporous structure are being formed by additive manufacturing. This allows for a positive controlled process having the desired characteristics of porosity over the whole volume of the microporous structure. It is a huge advantage with respect to other technologies that use negative manufacturing, like etching, which usually work from a surface only and provide only limited control with respect to characteristics deep within the volume.

Expediently, the additive manufacturing is performed on a base plane, preferably by 3-D printing. The base plane provides for a well-defined reference regarding orientation of the unit cells. Further, it allows for arranging the relative orientation of the unit cells to the base plane in such a manner that the unit cells are tilted such that all of its subelements are non-parallel to the base plane. This avoids formation of so called "horizontal" elements which are difficult to manufacture by 3-D printing.

It is further preferred that the unit cells are arranged in levels. This allows for an expedient manufacturing, in particular by 3-D printing. Further, this provides for a well-organized and regularly formed microporous structure, without defects. Further, thereby as scalable structure is created in which structures of increased thickness can easily be formed by providing additional levels.

Preferably, the unit cells are being configured such that they are connectable in series. This allows for an easy manufacturing of the microporous structure without any intermediate warpage. This is a huge benefit for providing a regularly formed microporous structure having controlled characteristics.

The pores are preferably sized in a range between 50 and 1500 μm. It has been found that this range provides for beneficial characteristics in terms of pore volume for storage and elution area for dispensing of the drugs in combination with implantable devices.

Preferably, in an embodiment that may deserve independent protection, the pores of the first size and the pores of the second size are being filled with different drugs. Importantly, by having the ratio between the elution areas predefined, it can be ensured that the different drugs are to be released at the appropriate respective rates. This is a distinct advantage which would not have been possible using an implant as discussed above in the prior art section. Further, by controlling the ratio between the volume of the pores of the first size and the pores of the second size not only the rates of dispensing the two different drugs can be controlled, but also it gives additional control with respect to the size of the drug storage in the pores, which in turn means control duration over which each of the respective drug shall be dispensed.

It is further preferred to configure the microporous structure such that cut-open pores are positioned at the surface. These cut-open pores are in direct communication with the surroundings of the microporous structure, and therefore a suitable for dispensing drugs that shall have immediate and strong effect. The cut-open pores provide for a maximum of immediate elution rate. Further, the cut-open pores can be filled with a different drug than used for filling the pores, like an infection drug for instant and aggressive infection suppression.

Preferably, the drugs are one or more selected from the group comprising hydrosoluble antibiotics (e.g. gentamicinsulfate, vancomyicinhydrochloride or similar).

Further preferably, the drugs may be deposited into the microporous structure by spraying, dipping, fogging or similar or advanced techniques like iontophoresis. Moreover, that drug can be deposited by using a carrier like hyaluronic acid, in particular with respect to the cut-open pores at the surface but also to the pores deep within the microporous structure for longer duration of dispensing.

The invention further relates to an implantable drug-eluting device comprising a microporous structure, the microporous structure comprising regularly arranged pores, wherein the pores are configured for receiving a drug and are being connected by interconnections, the interconnections originating from the pores having a first elution area, the interconnections being configured to convey the drug to a surface of the microporous structure for elution to surrounding tissue via the elution areas, characterized in that at least some of the pores are located at a surface of the microporous structure and are being cut at least partially open. Preferably, the microporous structure is of the cuboctaeder or fluorite-type. Preferably, the microporous structure is configured such that cut-open pores are positioned at the surface. These cut-open pores are in direct communication with the surroundings of the microporous structure, and therefore a suitable for dispensing drugs that shall have immediate and strong effect. The cut-open pores provide for a maximum of immediate elution rate. Further, the cut-open pores can be filled with a different drug than used for filling the pores, like an infection drug for instant and aggressive infection suppression.

The invention further relates to a corresponding method for manufacturing the implantable drug-eluting device.

Figure 3:
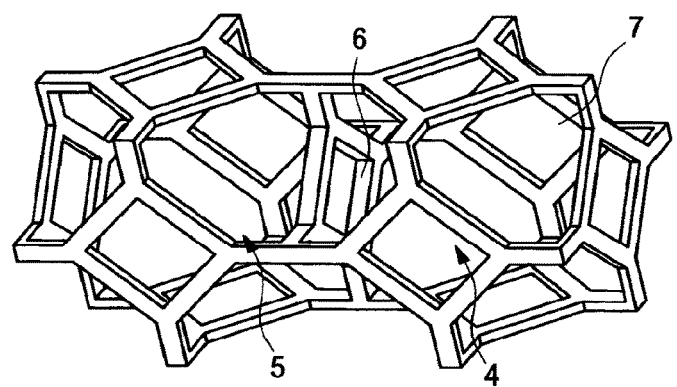
Figure 4:
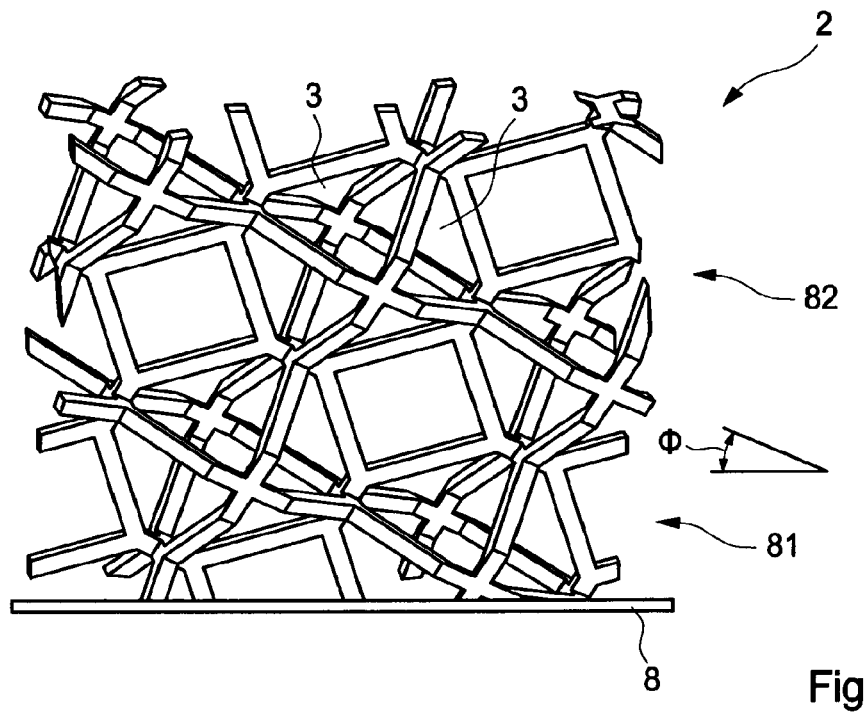
Figure 5:
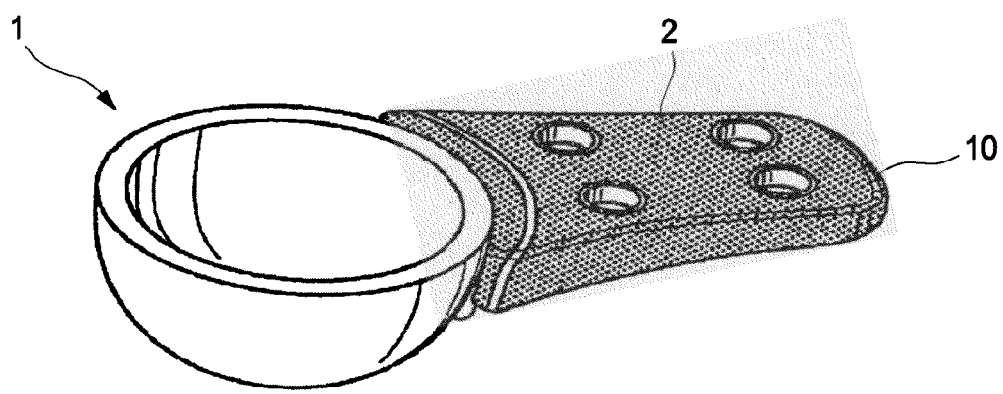
Figure 5:
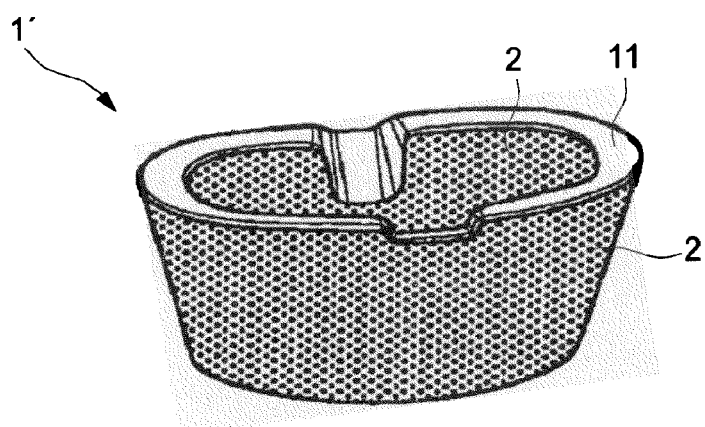
Figure 6:
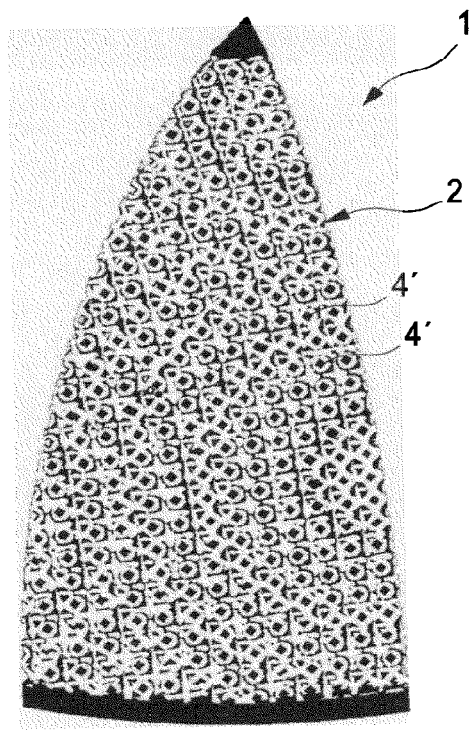
Figure 7:
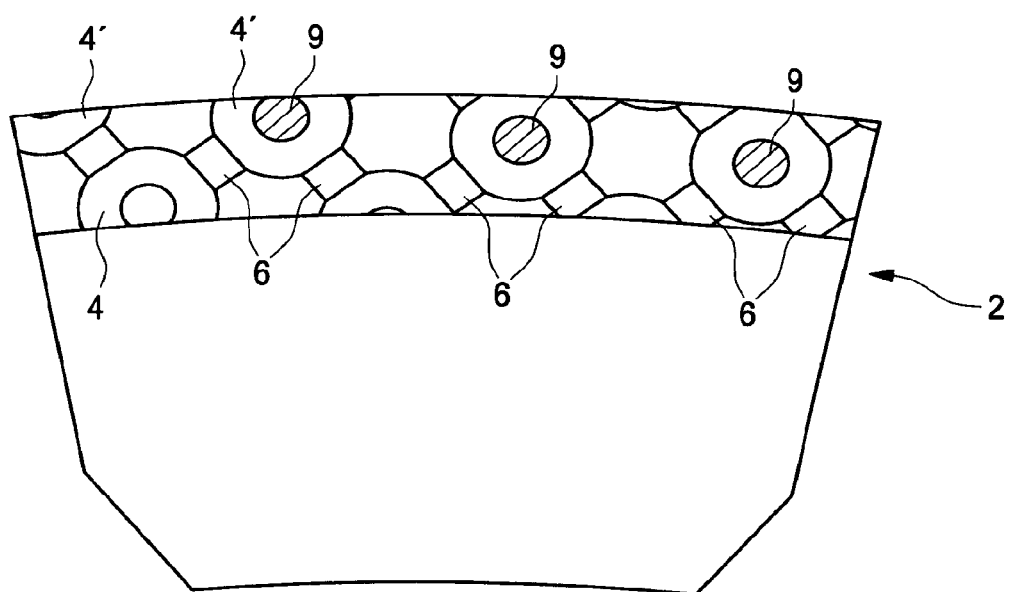

The invention will be further explained by the drawing using an illustrative embodiment as an example. The drawing comprises:

FIG. 1a, b a skeleton and a bodied view of the first example of the unit cell employing a basic type of a modified cuboctaeder comprising square and triangle shaped subelements;

FIG. 2a, b a skeleton and a bodied view of a second example of the unit cell employing an advanced type of the modified cuboctaeder comprising square subelements and subelements of a clipped triangle type;

FIG. 3 two unit cells connected in series;

FIG. 4 a view of a plurality of unit cells connected in series;

FIG. 5a, b two examples for implantable drug-eluting devices;

FIG. 6 a top-view of an implant comprising a microporous structure having cut-open pores at the surface; and FIG. 7 a cross-section showing configuration of the pores at the surface.

A porous structure 2 to be used for an implantable drug eluting device according to an embodiment of the invention is shown in FIGS. 1 to 4.

Figure 2:
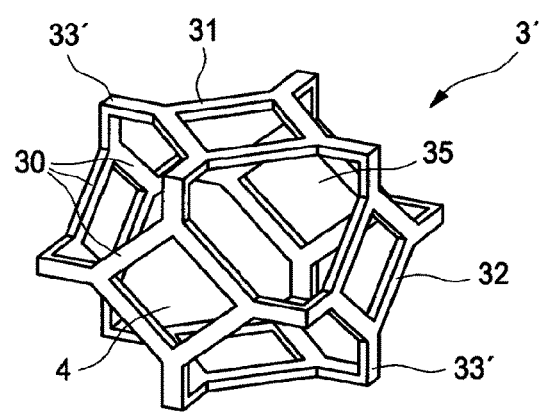
Figure 1:
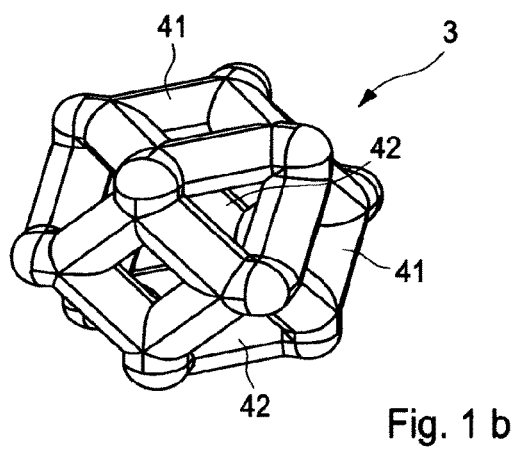
Figure 2:
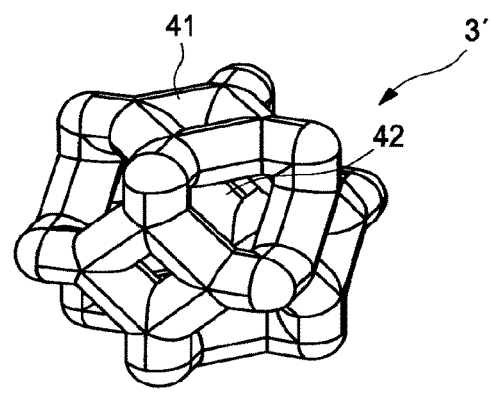

The microporous structure 2 is comprised of unit cells 3 which are arranged in a regular manner. Detailed views of two embodiments of unit cells 3, 3' are shown in FIGS. 1 and 2. FIG. 1 shows a unit cell of a modified cuboctaeder type. A cuboctaeder is a polyhedron with 14 faces, of which are six square faces and eight triangular faces. The normal or basic form of a cuboctaeder is formed by a plurality of bars 30 to form square subelements 31 and triangle subelements 32.

The embodiment as shown in FIG. 1 is a modified cuboctaeder featuring additional angled struts 33 mounted at the corners of the square subelements 31 to project diagonally outward. By virtue of this, the area of the square subelements 31 is decreased, whereas the area of the adjacent triangular subelements 32 is to be increased. Moreover, the triangular subelements 32 are modified in that the tips of the triangle giving the subelement its shape are clipped. FIG. 1a shows a skeleton model for providing a better visualization of the geometric elements and the spatial orientation with respect to each other, whereas FIG. 1b shows the fully bodied version of the elementary cell with subelements 31, 32 of proper thickness, thereby providing a more realistic impression of the thickness of the elements in relation to the free area therebetween and to the volume of the elementary cell 3.

Accordingly, the relation of the open area circumscribed by the square subelement 31 to the open area circumscribed by the triangle type subelement 32 is one (unity), i. e. despite their difference in shape the size of the areas circumscribed by the square subelement 31 and by the triangle type subelements 32 is identical.

An alternative embodiment of the elementary cell 3' is shown in FIG. 2. It is a variant of the embodiment shown in FIG. 1. Like elements are being provided with the same reference numerals. The main difference between the elementary cell 3 and the alternative elementary cell 3' is that the angled struts 33' of the alternative embodiment are increased in length. Thereby the area of the square subelements 31' is further decreased, whereas the area of the triangle type subelements 32' is substantially increased. FIG. 2b shows again a fully bodied version. In this alternative embodiment the relation of the open area circumscribed by the square subelement 31' to the open area circumscribed by the triangle type subelement 32' is just 0.2, that means the triangle type area is 5 times larger than the area of the square.

Now switching to FIGS. 3 and 4, there is shown that the unit cells 3, 3' are to be connected in series. The connection is made such that adjacent unit cells are to be connected via their angled struts 33 such that the adjacent unit cells 3, 3' will be oriented parallel with respect to each other. Thereby, the unit cells 3, 3' can be easily arranged in levels. It is to be noted while it is usually preferably that the unit cells are all of the same type (either unit cells like unit cells 3 shown in FIG. 1 or unit cells like unit cells 3' shown in FIG. 2), but this is not an absolute necessity. A variation of the unit cells between layers (inter-layer) and within layers (intra-layer) is possible.

A detailed view of two series-connected unit cells of the alternative embodiment 3' is shown in FIG. 3, whereas FIG. 4 shows a portion of the structure formed by a plurality of unit cells 3 arranged in a multi-level configuration. It is to be noted that adjacent pores 4, 5 are communicating with each other by interconnects 6, 7. The cross-section of each of these interconnects 6, 7 is defined by the open area of the respective square subelement 31 of triangle type subelement 32. The larger this area the wider is the interconnection, and as a result the rate of which a drug placed within the pores can flow through said interconnection is increased, too. Therefore, the open area of the interconnections 6 defined by the square subelements 31 is defined to be a first elution area, and correspondingly the open area of the interconnections 7 defined by the triangle type subelements 32 is defined to be a second elution area.

The unit cells 3, 3' are preferably formed by an additive process, in particular by means of 3D printing. An example for such an additive process is an Electron Beam Melting (EBM) process. This is an additive process used for manufacturing and may produce solid or porous structure. The powder of the desired material is provided in the desired granulometry. A base plane 8 is provided which serves as a horizontal plane on which the structure is to be formed by the EBM process. The base plane 8 could be a distinct element or it can be a surface of an object on which the porous structure shall be formed, like the base body of an implant 1 (see FIGS. 5a and b).

By the EBM process powders of the desired materials are deposited in successive layers 81, 82 (only the two lowermost layers are shown for clarity) at the desired positions in the desired sequence (as defined in a preceding modeling step for the porous structure) and made to melt such as to form a coherent body. A quite important advantage of the structure according to the present invention is that due to a tilting angle Φ all elements to be formed are non-parallel to the base plane 8. In the case of the base plane 8 being oriented horizontally (the normal case) this has a huge advantage in that all structural elements which are to be formed for the layers of unit cells are either oriented vertical or angled, but none is oriented horizontally. Generally speaking, additive processing has difficulties with manufacturing of strictly horizontal elements, and this difficulty is avoided owing to the tilt angle Φ.

Examples for implants 1, 1' which are provided with the microporous structure according to the present invention are shown in FIG. 5a, b. The first example shown in FIG. 5a is an implant 1 which may be an acetabular cup of the hip prosthesis. It is provided with a wing-like extension 10 for better fixation, and said wing-like extension 10 is being provided with the microporous structure 2 according to the present invention. The other example shown in FIG. 5B is a tibial cone 1' for augmenting the tibial component of a knee prosthesis. The tibial cone 1' features a hollow body encircled by a massive wall 11 for providing strength and acting as a shield against traversing of cement or other debris from the interior to the exterior of the tibial cone 1'. On both sides, the interior as well as exterior side of the massive wall 11 the microporous structure 2 according to the present invention is to be applied.

The configuration of the surface of such an implant 1 is shown in FIGS. 6 and 7. As it can be clearly seen in the uppermost portion of FIG. 7, the pores 4 (only pores of the first type are being shown for clarity) are being interconnected by the interconnections 6, and pharmaceutically active matter (drug) 9 is positioned within the pores 4. The pharmaceutically active matter (drug) 9 can leave the pores 4 via the interconnections 6, whose cross-section area is defining a rate of elution.

There are at least some pores 4' which are located just at the surface of the microporous structure 2, these pores being at least partially cut open (see in particular the left half of FIG. 6). The drug 9 placed in these pores 4' can leave the pores directly without being funneled through the interconnections 6, and therefore a much greater rate of elution will result. This allows for a rapid delivery of drugs 9 immediately subsequently to implantation of the prosthesis by using the cut-open pores 4' which are present at the surface of the microporous structure 2.

The method for manufacturing the implantable drug-eluting device comprises a body forming as implant proper, on which the porous structure is to be formed there. The method comprises the steps of using the body as a base plane 8, depositing a layer of a plurality of regularly arranged elementary cells 3, thereby forming pores 4, 5 of the first and the second size, the pores being communicating with each other by interconnections having a first elution area and respective second elution area, depositing a second and further layer of a plurality of regularly arranged elementary cells 3 as required, wherein a ratio between the first elution area 34 and the second elution area 35 is predefined and selectable. Preferably, a surface of the microporous structure is created, wherein preferably the surface at least provides some cut-open pores 4', and placing at least one type of drug 9 in the pores 4, 5. Preferably, in the pores of the first size 4 a different drug is placed than in the pores of the second size 5. Further preferably, the layers are arranged such that they are oriented non-parallel to the base plane 8.

The invention claimed is:

1. A microporous structure, the microporous structure comprising: unit cells, the unit cells comprising a plurality of bars, angled struts projecting diagonally outwards from the unit cells, and openings; the openings forming regularly arranged pores in at least two different uniform sizes, a first size and a second size, wherein the pores are configured for receiving a drug and are being connected by interconnections, the interconnections originating from the pores of the first size having a first elution area and the interconnections originating from the pores of the second size having a second elution area, the interconnections being configured to convey the drug to a surface of the microporous structure for elution to surrounding tissue via the elution areas, wherein said first elution area and said second elution area are differently sized, and said first and second elution areas determine a rate of elution of any drug in the respective pores, and a ratio between the first elution area and the second elution area is predefined and selectable, wherein the microporous structure is a modified cuboctaeder comprising square and triangle type subelements, the square type subelements being connected by additional angled struts, wherein the triangle type subelements comprise a clipped shape.

2. The microporous structure of claim 1, wherein a ratio between a volume of the pores of the first size and the pores of the second size is predefined and selectable.

3. The microporous structure of claim 1, wherein said ratio of elution area is substantially equal but the ratio between a volume of the pores of the first size and the pores of a second size differs at least by factor 2.

4. The microporous structure of claim 1, wherein said ratio between a volume of the pores of the first size and the pores of the second size is smaller than 2 but the ratio between the first elution area and the second elution area differs at least by 4.

5. The microporous structure of claim 1, wherein the microporous structure is formed by additive manufacturing.

6. The microporous structure of claim 1, wherein the unit cells are arranged in levels and the unit cells are connectable in series.

7. The microporous structure of claim 1, wherein the pores are sized in a range between 50 and 1500 μm.

8. The microporous structure of claim 1, wherein the pores of the first size and the pores of the second size may be filled with different drugs.

9. The microporous structure of claim 1, wherein drugs are deposited in the pores, wherein the drug is a hydro-soluble antibiotic, and wherein the drugs are deposited by means of a carrier.

10. The microporous structure of claim 1, wherein at least some of the pores are located at a surface of the microporous structure and are being cut at least partially open.

11. The microporous structure of claim 1, wherein the drug is selected from the group consisting of gentamicinsulfate and vancomyicinhydrochloride.

12. The microporous structure of claim 1, wherein the microporous structure is formed by additive manufacturing on a base plane.

13. The microporous structure of claim 12, wherein the microporous structure comprises unit cells, wherein the unit cells are tilted such that all of its subelements are non-parallel to the base plane.

14. The microporous structure of claim 1, wherein the modified cuboctaeder comprises square type subelements forming six square faces, the triangle type subelements forming eight triangular faces.

15. The microporous structure of claim 1, wherein at least some of the pores are located at a surface of the microporous structure and are being cut at least partially open, wherein the cut-open pores comprise a second drug that is different from the first drug.

16. A method for manufacturing the microporous structure of claim 1, which further comprises a body forming an implant proper, on which the microporous structure is to be formed there, the method comprising the steps of:
using the body as a base plane;
depositing a layer of a plurality of regularly arranged elementary cells, thereby forming pores of the first and the second size, the pores being communicating with each other by interconnections having a first elution area and respective second elution area;
depositing a second and further layer of a plurality of regularly arranged elementary cells as required; and
forming a surface of the microporous structure, wherein a ratio between the first elution area and the second elution area is predefined and selectable.

17. The method of claim 16, characterized by forming an implant.

* * * * *